US006187302B1

(12) United States Patent
Nguyen et al.

(10) Patent No.: US 6,187,302 B1
(45) Date of Patent: Feb. 13, 2001

(54) MULTI-COMPONENT REDUCING AGENT AND PROCESS FOR PERMANENTLY RESHAPING THE HAIR USING THIS AGENT

(75) Inventors: Ly-Lan Nguyen, L'Hay les Roses; Anne Sabbagh, Rueil Malmaison, both of (FR)

(73) Assignee: L'Oreal S.A., Paris (FR)

( * ) Notice: Under 35 U.S.C. 154(b), the term of this patent shall be extended for 0 days.

(21) Appl. No.: 09/221,970

(22) Filed: Dec. 29, 1998

(30) Foreign Application Priority Data

Dec. 30, 1997 (FR) .................................................. 97 16717

(51) Int. Cl.⁷ ....................................................... A61K 7/09
(52) U.S. Cl. ........................ 424/70.1; 424/70.2; 424/70.5; 424/70.51
(58) Field of Search .................................. 424/70.2, 70.5, 424/70.51; 8/410, 411

(56) References Cited

U.S. PATENT DOCUMENTS

| 4,749,732 | 6/1988 | Kohl et al. ............................. 524/43 |
| 5,935,560 | * 8/1999 | Seper et al. ......................... 424/70.12 |

FOREIGN PATENT DOCUMENTS

| 4 317 663 | 12/1994 | (DE) . |
| 0 227 994 | 7/1987 | (EP) . |
| 0 295 780 | 12/1988 | (EP) . |
| 0 362 663 | 4/1990 | (EP) . |
| 1 530 369 | 6/1968 | (FR) . |
| 2 535 730 | 5/1984 | (FR) . |
| 0 377 836 | 7/1990 | (FR) . |
| 2 673 197 | 8/1992 | (FR) . |
| 2 730 100 | 8/1996 | (FR) . |
| WO 92/05674 | 4/1992 | (WO) . |
| WO 94/07844 | 4/1994 | (WO) . |
| WO 97/04738 | 2/1997 | (WO) . |

OTHER PUBLICATIONS

Kristi J. Robson et al., "6–Hydroxy–4–sphingenine in human epidermal ceramides", Journal of Lipid Research, vol. 35, No. 11, Nov. 1994, pp. 2060–2068.
English Language Derwent Abstract of DE 4 317 663.
English Language Derwent Abstract of EP 0 362 663.
English Language Derwent Abstract of FR 1 530 369.
English Language Derwent Abstract of FR 2 535 730.
English Language Derwent Abstract of FR 2 673 197.
English Language Derwent Abstract of FR 2 730 100.

* cited by examiner

Primary Examiner—Shelley A. Dodson
Assistant Examiner—Konata M George
(74) Attorney, Agent, or Firm—Finnegan, Henderson, Farabow, Garrett & Dunner, L.L.P.

(57) ABSTRACT

The invention relates to a reducing agent intended to be used in a process for permanently reshaping the hair, this agent comprising:

a first component comprising at least one thiol-bearing reducing agent in aqueous medium, and a second component comprising at least one thickening polymer in aqueous medium, said thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid;

wherein the first and second components are to be mixed with each other at the time of initiating the permanently reshaping of the hair to obtain a ready-to-use reducing composition.

29 Claims, No Drawings

MULTI-COMPONENT REDUCING AGENT AND PROCESS FOR PERMANENTLY RESHAPING THE HAIR USING THIS AGENT

The invention relates to a reducing composition, i.e. agent, containing at least two components, comprising a first composition containing a reducing agent in an aqueous solution and a second composition containing a specific thickener. The two compositions are mixed together close to the time of use, preferably immediately before the time of use, to form a ready-to-use mixture, and the mixture is used in a process for treating the hair to permanently reshape it. The invention also relates to processes for using this agent.

One technique commonly used in the cosmetics field for imposing a long-lasting shape on the hair involves reshaping the hair using a reducing agent and then an oxidizing agent.

The technique most commonly used to permanently reshape the hair involves, as a first step, opening the cystine disulfide (S-S) linkages of keratin (cystine) using a composition containing a reducing agent, and then, after the hair has been treated, the hair is preferably rinsed. The second step involves reforming the said disulfide linkages by applying to the hair, which has been placed under tension beforehand, with curlers or the like, or which has been shaped or smoothed out by other means, an oxidizing composition also known as a "fixer", so as to give the hair the desired final shape.

This technique thus makes it possible either to make the hair wavy or to straighten it or remove curls therefrom, or alternatively to make it smooth.

The new shape given to the hair by a chemical treatment is long-lasting, i.e., lasting for a few weeks, and is resistant in particular to washing with water or with shampoo. This is in contrast with techniques using styling products which lead to a temporary reshaping, such as hairsetting, such a reshaping disappearing after styling or shampooing.

The reducing compositions generally used for the first step of a permanent-waving operation contain sulfites, bisulfites or, preferably, thiols as reducing agents. Among these preferred reducing agents are cysteine and its derivatives, cysteamine and its derivatives, thiolactic acid and thioglycolic acid and its esters, in particular glyceryl thioglycolate. Thioglycolic acid is particularly effective and constitutes the product most frequently used to reduce the disulfide linkages of keratin.

For certain permanent-waving techniques, such as, for example, in reshaping processes without curlers, or in a hair-straightening process, it is preferable to use sufficiently thickened reducing agents in order to facilitate their application, to allow better localization of the product on the hair, to avoid any running of the reducing composition and to allow the hair to be held in the desired position.

However, the formulation of thickened reducing agents is particularly difficult because of frequent problems of instability over time. Several phenomena generally occur: a fall in viscosity of the product and/or a decrease in the reducing agent titer, and/or the appearance of an unpleasant odor, or all of these shortcomings at the same time, are frequently observed in particular.

If the thickening system is separated from the reducing agent for keratin fibers, for example in a multi-compartment system or kit, the difficulty of obtaining a uniform thickening quickly enough and easily enough after mixing is encountered.

Broadly, the invention can solve these various problems by providing a reducing agent containing two components, comprising a first component comprising a thiol-bearing reducing agent in aqueous solution and a second component comprising a composition containing a thickening polymer in a specific form.

In one aspect, the invention provides a reducing composition for permanently reshaping the hair comprising:
  a first component comprising at least one thiol-bearing reducing agent in aqueous medium, and
  a second component comprising at least one thickening polymer in aqueous medium, the thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid;
wherein the first and second components are to be mixed with each other at the time of initiating said permanently reshaping of the hair to obtain a ready-to-use reducing composition.

In another aspect, the invention provides a ready-to-use reducing composition for permanently reshaping the hair formed by mixing at or close to the time of initiating the permanently reshaping of the hair:
  a first component comprising at least one thiol-bearing reducing agent in aqueous medium, and
  a second component comprising at least one thickening polymer in aqueous medium, said thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid.

In yet another aspect, the invention provides a process for permanently reshaping the hair, comprising the steps:
  obtaining, at or close to the time of said subsequent applying step, a ready-to-use reducing composition by mixing
    a first component comprising at least one thiol-bearing reducing agent in aqueous medium, and
    a second component comprising at least one thickening polymer in aqueous medium, the thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid;
  applying to the hair, before, during or after the step of placing the hair under tension by a mechanical means or shaping by any manual means, the ready-to-use reducing composition thus obtained;
  leaving the ready-to-use composition on the hair for a period of time sufficient to reduce the disulfide linkages of the hair;
  optionally rinsing;
  thereafter applying to the hair a fixing composition containing at least one oxidizing agent;
  leaving the fixing composition on the hair for a period of time sufficient to allow permanent reshaping; and
  thereafter rinsing the hair.

The compositions of the present invention have the advantage in particular of being very easy and quick to prepare, thereby making it possible to obtain a thickened and uniform reducing composition almost immediately, by simple mixing of the two components.

Furthermore, the reducing composition of the invention has a texture which is particularly suited to all applications and in particular to applications to the hair which is not wound on curlers; since this composition is easy to apply, it does not run and it allows the hair to be held in the desired position.

Other subjects of the invention will become apparent on reading the description and the examples which follow.

As described above, the first component and the second component are intended to be mixed with each other at the time of use in order to obtain a ready-to-use reducing composition intended to be applied to the hair in order to reduce the hair's disulfide linkages.

Preferably, the reducing agent is chosen from thioglycolic acid, thiolactic acid, cysteine, cysteamine, thioglycerol and glyceryl thioglycolate or one of the cosmetically acceptable salts thereof, such as, more particularly, the hydrochlorides, hydrobromides, citrates, acetates and sulfates.

The reducing agent is used in proportions which are sufficient to reduce the disulfide linkages, and preferably in proportions ranging from 1 to 25%, in particular from 3 to 25%, by weight relative to the total weight of the ready-to-use composition.

The thickening polymers in the second component are preferably chosen from
- ammonium acrylate/acrylamide copolymers, as a W/O reverse emulsion, such as Bozepol C sold by Hoechst;
- acrylamide/2-acrylamidomethylpropanesulfonic copolymers, as a reverse emulsion, such as Sepigel 305 sold by SEPPIC;
- sodium acrylate/acrylamide copolymers, as a reverse emulsion, such as Sepigel 901 sold by SEPPIC;
- copolymers of trimethylethylammonium methacrylate chloride/acrylate, as a dispersion in oil, such as Salcare SC 92 sold by Allied Colloids;
- homopolymers of crosslinked ethyltrimethylammonium methacrylate chloride, as a dispersion in oil, such as Salcare SC 95 sold by Allied Colloids;
- hydroxypropylmethylcellulose, as an aqueous dispersion, such as AQU D-3295A sold by Hercules.

The thickening polymer is present in the second component in proportions such that the ready-to-use composition resulting from mixing the first and second components has a sufficient viscosity to prevent or reduce running on the scalp and/or in order to maintain the reshaping of the hair.

The thickening polymers preferably represent from 0.1 to 30% by weight relative to the total weight of the ready-to-use composition.

The first component and/or the second component mentioned above can also contain one or more alkaline agents.

The alkaline agents can be chosen in particular from monoethanolamine, diethanolamine, triethanolamine, isopropanolamine, 1,3-propanediamine, an ammonium or alkali metal carbonate or bicarbonate, an organic carbonate such as guanidine carbonate or an alkali metal hydroxide, used alone or as a mixture.

The pH of the first component and that of the second component can be adjusted so as to obtain a pH of the ready-to-use composition ranging from 7.0 to 11.0.

The reducing agent can also contain, either in its first component or in its second component, or in the ready-to-use mixture, surfactants and treating agents, such as anionic, nonionic or amphoteric agents.

The surfactants used are those commonly used in permanent-waving reducing compositions and can be nonionic, anionic, cationic or amphoteric. Preferred surfactants are chosen from alkyl sulfates, alkylbenzene sulfates, alkyl ether sulfates, alkyl sulfonates, quaternary ammonium salts, alkylbetaines, oxyethylenated alkylphenols, fatty acid alkanolamides, oxyethylenated fatty acid esters and nonionic surfactants of the hydroxypropyl ether family.

These surfactants are generally used in proportions such that, in the composition resulting from mixing the first and second components, their maximum proportion is about 30% by weight, and preferably from 0.5 to 10% by weight, relative to the total weight of the composition.

The treating agents which can be used are volatile or non-volatile, linear or cyclic silicones or mixtures thereof, polydimethylsiloxanes, quaternized polyorganosiloxanes, those described in French patent application 2,535,730 (the disclosure of this and all other patent and technical documents cited below are specifically incorporated by reference herein), polyorganosiloxanes containing an aminoalkyl radical which are modified with alkoxycarbonylalkyl groups, as described in U.S. Pat. No. A4,749,732, poyorganosiloxanes such as polydimethylsiloxane/polyoxyalkyl copolymers, such as dimethicone copolyol, polydimethylsiloxanes containing stearoxy end groups (stearoxydimethicone), polydimethylsiloxane/dialkylammonium acetate copolymers or polydimethylsiloxane/polyalkyltin copolymers described in GB-A-2,197,352, polysiloxanes organomodified with mercapto or mercaptoalkyl groups, as described in FR-B-1,530,369 and EP-A-0,295,780, and silanes such as stearoxytrimethylsilane.

Other treating agents can also be used, such as waxes, polymers chosen from cosmetically acceptable polymers which can be cationic, anionic, nonionic or amphoteric polymers, swelling and penetrating agents which allow the efficacy of the reducing agent to be reinforced, such as dimethylisosorbitol, urea and its derivatives, pyrrolidone, n-alkylpyrroiidone, thiamorpholinone, alkyl ethers of alkylene glycol or of dialkylene glycol, such as, for example, propylene glycol monomethyl ethyl ether, dipropylene glycol monomethyl ether, $C_3$–$C_6$ alkanediols such as, for example, 1,2-propanediol, 2-imidazolidinone, and other compounds such as fatty alcohols, lanolin derivatives, ceramides and in particular ceramides themselves, the glycoceramides and pseudoceramides described in particular in FR-A-9511399 and in Downing, Journal of Lipid Research, Vol. 35, p. 2060, 1994, or in FR-A-2,673,197, EP-A-0,227, 994, WO-94/07844 and WO-92/05674, active ingredients such as pantothenic acid and panthenol, agents for preventing hair loss, antidandruff agents, suspending agents, sequestering agents, opacifiers, dyes, sunscreens, fragrances and preserving agents.

Before use, the first component defined above is mixed with the second component defined above.

Preferably, 1 to 99% by weight and in particular 60 to 98.5% by weight, relative to the total weight, of the first component containing a reducing agent is mixed with 99 to 1 % and in particular 1.5 to 40% by weight of the second component containing a thickening polymer as an aqueous or oily dispersion or as a reverse emulsion.

In one process in accordance with the invention
- a composition containing a reducing agent as defined above in aqueous medium is premixed with a composition containing a thickening polymer as an aqueous or oily dispersion or as a reverse emulsion as defined above;
- the composition thus obtained is applied to wet or dry hair before, during or after the step of placing the hair under tension by a mechanical means or shaping by any manual means;

after leaving the composition on the hair for a period of time which is sufficient to allow the reduction of the disulfide linkages of the hair, and after an optional rinsing, a fixing composition containing at least one oxidizing agent is applied;

after leaving the fixing composition on the hair for a sufficient period of time, a final rinsing is carried out.

The step of placing the hair under tension can be carried out by any suitable and known mechanical means, such as, for example, rollers, curlers, etc.

It is also possible to carry out the process without using equipment for placing the hair under tension, i.e. by simply applying the composition using the fingers or a comb, which allows the hair to be sculpted in order to maintain it in a desired position, such as curls, waves or spikes.

According to an optional step of the process of the invention, after applying the reducing composition, the hair can be subjected to a heat treatment by heating to a temperature ranging from 30 to 60°C. This heating optionally allows the final degree of curliness of the hair to be adjusted.

In practice, this operation can be carried out using a hairdressing hood, a hairdryer, an infrared radiation emitter and other standard heating equipment.

Needless to say, it is also possible to work at room temperature.

According to a specific embodiment of the invention, it is possible not to carry out the rinsing step after reduction, in particular when the hair has been shaped by means other than mechanical means.

In general, before carrying out the rinsing or the application of the oxidizing composition, the hair onto which the reducing composition has been applied is left to stand for a few minutes, generally ranging from 2 to 30 minutes and preferably from 5 to 20 minutes, to give the reducing agent a good amount of time to act correctly on the hair.

Preferably, during this waiting period, care should be taken to ensure that the hair does not dry out completely and thus remains damp until the next step is started. To achieve this, bonnets or protective gels can thus be used.

The oxidizing agents which can be used in the fixing compositions can be chosen in particular from hydrogen peroxide or aqueous hydrogen peroxide solution, urea peroxide, alkali metal bromates, persalts such as perborates and persulfates, and enzymes such as peroxidases andoxidoreductases with two unpaired electrons. It is particularly preferred to use hydrogen peroxide or enzymes.

The concentration of aqueous hydrogen peroxide solution can range from 1 to 10 volumes but is preferably about 8 volumes.

The concentration of alkali metal bromates is from 1 to 12% and that of persalts is from 0.1 to 15% by weight relative to the total weight of the oxidizing composition.

The pH of the oxidizing composition can range from 2 to 7 and is preferably from 3 to 6, in particular in the case of aqueous hydrogen peroxide solution.

The aqueous hydrogen peroxide solution can be stabilized, for example with phenacetin, acetaniline, mono- and trisodium phosphates or with 8-hydroxyquinoline sulfates.

The fixing or oxidizing compositions can, in addition, also contain alkaline agents, surfactants or treating agents as defined above.

In the case in which the hair has been placed under tension by a mechanical means, the mechanical means or the curlers and the like which held the hair under tension in the desired shape throughout the treatment can be removed from the hair before or after the fixing step.

The period of time for which the fixing composition is left on the hair can preferably range from 5 to 30 min, and, more preferably, from 5 to 15 min.

The examples which follow are intended to illustrate the invention without, however, limiting the scope.

EXAMPLE 1

| 1) Part A | |
|---|---|
| Sepigel 305 (SEPPIC) (sodium acrylate/acrylamide copolymer as a reverse emulsion in isoparaffin/water) | 15 g |
| 2) Part B | |
| Thioglycolic acid | 9 g |
| Diethylenetriaminepentaacetic acid, pentasodium salt, as an aqueous 40% solution | 0.4 g |
| Aqueous ammonia qs | pH 8.4 |
| Fragrance | 0.5 g |
| Oxyethylenated (20 EO) oleyl alcohol | 1 g |
| Demineralized water qs | 85 g |

At the time of use, part A and part B are introduced into a shaker. The mixture is shaken and a uniform creamy white gel which is ready for use is obtained immediately.

EXAMPLE 2

| 1) Part A | |
|---|---|
| Bozepol C (Hoechst) (ammonium acrylate/acrylamide copolymer (95/5) as a W/O reverse emulsion) | 6 g |
| 2) Part B | |
| Thiolactic acid | 5 g |
| Diethylenetriaminepentaacetic acid, pentasodium salt, as an aqueous 40% solution | 0.2 g |
| Aqueous ammonia qs | pH 7.9 |
| Ammonium carbonate | 5 g |
| Fragrance | 0.5 g |
| Oxyethylenated (20 EO) oleyl alcohol | 1 g |
| Demineralized water qs | 85 g |

At the time of use, part A and part B are introduced into a shaker. The mixture is shaken and a uniform creamy white gel which is ready for use is obtained immediately.

What is claimed is:

1. A reducing composition for permanently reshaping the hair comprising:

a first component comprising at least one thiol-bearing reducing agent in aqueous medium, and a second component comprising at least one thickening polymer in aqueous medium, said thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid;

wherein said first and second components are to be mixed with each other at the time of initiating said permanently reshaping of the hair to obtain a ready-to-use reducing composition.

2. A ready-to-use reducing composition for permanently reshaping the hair formed by mixing at or close to the time of initiating said permanently reshaping of the hair:

a first component comprising at least one thiol-bearing reducing agent in aqueous medium, and a second component comprising at least one thickening polymer in aqueous medium, said thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid.

3. The reducing composition of claim 1, wherein said thickening polymer is chosen from ammonium acrylate/acrylamide copolymers, acrylamide/2-acrylamidomethylpropanesulfonic copolymers, sodium acrylate/acrylamide copolymers, trimethylethylammonium methacrylate chloride/acrylate copolymers, crosslinked ethyltrimethylammonium methacrylate chloride homopolymers and hydroxypropylmethylcellulose.

4. The reducing composition of claim 1, wherein said at least one thiol-bearing reducing agent in the first component is chosen from thioglycolic acid, thiolactic acid, cysteine, cysteamine, glyceryl thioglycolate, thioglycerol and cosmetically acceptable salts thereof.

5. The reducing composition of claim 4, wherein said cosmetically acceptable salts are chosen from hydroclorides, hydrobromides, citrates, acetates, and sulfates.

6. The ready-to-use reducing composition of claim 2, wherein said at least one thiol-bearing reducing agent represents from 1 to 25% by weight relative to the total weight of the ready-to-use reducing composition.

7. The ready-to-use reducing composition of claim 6, wherein said at least one thiol-bearing reducing agent represents from 3 to 25% by weight relative to the total weight of the ready-to-use reducing composition.

8. The ready-to-use reducing composition of claim 2 wherein said thickening polymer ranges from 0.1 to 30% by weight relative to the total weight of the ready-to-use reducing composition.

9. The ready-to-use reducing composition of claim 2, further comprising at least one alkaline agent.

10. The ready-to-use reducing composition of claim 9 wherein said at least one alkaline agent is chosen from monoethanolamine, diethanolamine, triethanolamine, isopropanolamine, 1,3-propanediamine, ammonium carbonates, ammonium bicarbonates, alkali metal carbonates, alkali metal bicarbonates, guanidine carbonates, and alkali metal hydroxides.

11. The ready-to-use reducing composition of claim 2, wherein said composition has a pH ranging from 7.0 to 11.0.

12. The reducing composition of claim 1, wherein said composition additionally contains at least one surfactant chosen from anionic, nonionic, cationic and amphoteric surfactants.

13. The reducing composition of claim 12, wherein said at least one surfactant is chosen from alkyl sulfates, alkylbenzene sulfates, alkyl ether sulfates, alkyl sulfonates, quaternary ammonium salts, alkylbetaines, oxyethylenated alkylphenols, fatty acid alkanolamides, oxyethylenated fatty acid esters and nonionic surfactants of the hydroxypropyl ether family.

14. The ready-to-use reducing composition of claim 2, wherein said composition additionally comprises at least one surfactant chosen from anionic, nonionic, cationic and amphoteric surfactants, and further wherein said at least one surfactant is present in an amount of about 30% by weight relative to the total weight of the ready-to-use reducing composition.

15. The ready-to-use reducing composition of claim 2, wherein said at least one surfactant represents from 0.5 to 10% by weight relative to the total weight of the ready-to-use reducing composition.

16. The ready-to-use reducing composition of claim 2, further comprising at least one treating agent chosen from silicones, waxes, polymers, swelling agents, penetrating agents, fatty alcohols, lanolin derivatives, ceramides, active ingredients, agents for preventing hair loss, antidandruff agents, suspending agents, sequestering agents, opacifiers, dyes, sunscreens, preserving agents and fragrances.

17. The ready-to-use reducing composition of claim 16, wherein said at least one treating agent is chosen from volatile and non-volatile, linear and cyclic silicones, polydimethylsiloxanes, quaternized polyorganosiloxanes, polyorganosiloxanes containing an aminoalkyl radical which are modified with alkoxycarbonylalkyl groups, polydimethylsiloxane/polyoxyalkyl copolymers, polydimethylsiloxanes containing stearoxy end groups, polydimethylsiloxane/dialkylammonium acetate copolymers, polydimethylsiloxane/polyalkyltin copolymers, polysiloxanes organomodified with mercapto groups, polysiloxanes organomodified with mercaptoalkyl groups, silanes, waxes, cosmetically acceptable polymers, swelling and penetrating agents, active ingredients, agents for preventing hair loss, antidandruff agents, suspending agents, sequestering agents, opacifiers, dyes, sunscreens, fragrances and preserving agents.

18. The reducing composition of claim 1, wherein said first component represents from 1 to 99% by weight relative to the total weight of the reducing composition.

19. The reducing composition of claim 18, wherein said first component represents from 60 to 98.5% by weight relative to the total weight of the reducing composition.

20. The reducing composition of claim 1, wherein said second component represents from 1 to 99% by weight relative to the total weight of the reducing composition.

21. The reducing composition of claim 20, wherein said second component represents from 1.5 to 40% by weight relative to the total weight of the reducing composition.

22. A process for permanently reshaping the hair, comprising the steps:

obtaining, at or close to the time of said subsequent applying step, a ready-to-use reducing composition by mixing a first component comprising at least one thiol-bearing reducing agent in aqueous medium, and a second component comprising at least one thickening polymer in aqueous medium, said thickening polymer being in the form of an aqueous dispersion, an oily dispersion, or a reverse emulsion, with the proviso that said thickening polymer is not vinylpyrollidone-styrol, carboxymethylcellulose, acrylic acid homopolymers, quaternary hydroxyethylcellulose, and cross-linked polymers of polymethacrylic acid;

applying to said hair, before, during or after the step of placing the hair under tension mechanically or shaping manually, the ready-to-use reducing composition thus obtained;

leaving the ready-to-use composition on the hair for a period of time sufficient to reduce the disulfide linkages of the hair;

optionally rinsing;

thereafter applying to said hair a fixing composition containing at least one oxidizing agent;

leaving the fixing composition on the hair for a period of time sufficient to allow permanent reshaping; and thereafter rinsing said hair.

23. The process of claim 22 wherein 1% to 99% by weight, relative to the total weight of the first and second components, of said first component comprising at least one thiol-bearing reducing agent in aqueous medium, is mixed with 99% to 1% by weight, relative to the total weight of the first and second components, of said second component comprising at least one thickening polymer in aqueous medium, said thickening polymer being in the form of an aqueous dispersion, an oily dispersion, or a reverse emulsion.

24. The process of claim 22, wherein the pH of the ready-to-use composition ranges from 7.0 to 11.0.

25. The process of claim 22, wherein said period of time in said step of leaving said ready-to-use composition on the hair for a period of time sufficient to reduce the disulfide linkages of the hair reducing composition is from 2 to 30 min.

26. The process of claim 22, wherein said optionally rinsing step is effected prior to said step of thereafter applying to said hair a fixing composition containing at least one oxidizing agent.

27. The process of claim 22, wherein said at least one oxidizing agent is chosen from hydrogen peroxide, urea peroxide, alkali metal bromates, persalts, and enzymes.

28. The process of claim 27 wherein said persalts are chosen from perborates and persulfates and said enzymes are chosen from peroxidases and oxidoreductases with two unpaired electrons.

29. The process of claim 22, wherein said step of thereafter rinsing said hair is carried out with water.

* * * * *

UNITED STATES PATENT AND TRADEMARK OFFICE
CERTIFICATE OF CORRECTION

PATENT NO. : 6,187,302 B1
DATED : February 13, 2001
INVENTOR(S) : Ly-Lan Nguyen et al.

Page 1 of 1

It is certified that error appears in the above-identified patent and that said Letters Patent is hereby corrected as shown below:

<u>Claim 5, column 7,</u>
Line 23, "hydroclorides" should read -- hydrochlorides --.

Signed and Sealed this

Thirtieth Day of October, 2001

Attest:

*Attesting Officer*

NICHOLAS P. GODICI
*Acting Director of the United States Patent and Trademark Office*